United States Patent
Seebauer et al.

(10) Patent No.: US 10,161,062 B2
(45) Date of Patent: Dec. 25, 2018

(54) COMPOSITION COMPRISING AN ENGINEERED DEFECT CONCENTRATION

(71) Applicant: The Board of Trustees of the University of Illinois, Urbana, IL (US)

(72) Inventors: Edmund G. Seebauer, Urbana, IL (US); Prashun Gorai, Lakewood, CO (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 175 days.

(21) Appl. No.: 15/134,560

(22) Filed: Apr. 21, 2016

(65) Prior Publication Data

US 2016/0319461 A1 Nov. 3, 2016

Related U.S. Application Data

(60) Provisional application No. 62/154,314, filed on Apr. 29, 2015.

(51) Int. Cl.
| | |
|---|---|
| C30B 31/08 | (2006.01) |
| C30B 29/16 | (2006.01) |
| H01L 31/0224 | (2006.01) |
| G01N 33/00 | (2006.01) |
| G01N 27/12 | (2006.01) |
| H01L 33/26 | (2010.01) |
| H01L 33/28 | (2010.01) |

(52) U.S. Cl.
CPC .............. *C30B 31/08* (2013.01); *C30B 29/16* (2013.01); *G01N 27/125* (2013.01); *G01N 33/0027* (2013.01); *H01L 31/022483* (2013.01); *H01L 33/26* (2013.01); *H01L 33/28* (2013.01); *H01L 33/285* (2013.01)

(58) Field of Classification Search
CPC ......... C30B 29/10; C30B 29/16; C30B 31/08; H01L 33/28; H01L 33/285
See application file for complete search history.

(56) References Cited

U.S. PATENT DOCUMENTS

| | | | |
|---|---|---|---|
| 2006/0024928 A1* | 2/2006 | Seebauer | H01L 21/306 438/514 |
| 2012/0172648 A1* | 7/2012 | Seebauer | B82Y 30/00 585/733 |

OTHER PUBLICATIONS

Barbier, A. et al., "Stability and stoichiometry of (polar) oxide surfaces for varying oxygen chemical potential", *Journal of Physics: Condensed Matter*, 20, 184014 (2008), pp. 1-13; doi:10.1088/0953-8984/20/18/184014.

Batzill, Matthias, "Fundamental aspects of surface engineering of transition metal oxide photocatalysts", *Energy Environ. Sci.*, 4 (2011) pp. 3275-3286; DOI:10.1039/c1ee01577j.

Brillson, L. J. et al., "Massive point defect redistribution near semiconductor surfaces and interfaces and its impact on Schottky barrier formation", *Physica B: Condens. Matter*, 404 (2009) pp. 4768-4773; doi:10.1016/j.physb.2009.08.151.

Calzolari, Arrigo et al., "Dipolar and charge transfer effects on the atomic stabilization of ZnO polar surfaces", *Surface Science*, 607 (2013) pp. 181-186.

Cowern, N.E.B. et al., "Impurity Diffusion via an Intermediate Species: The B-Si System", *Physical Review Letters*, 65, 19 (Nov. 5, 1990), pp. 2434-2437.

De Souza, Roger A. et al., "Using $^{18}O/^{16}O$ exchange to probe an equilibrium space-charge layer at the surface of a crystalline oxide: method and application", *Phys. Chem. Chem. Phys.*, 10 (2008) pp. 2356-2367.

Diebold, Ulrike, "The surface science of titanium dioxide", *Surface Science Reports*, 48 (2003) pp. 53-229.

Diebold, Ulrike et al., "Oxide Surface Science", *Ann. Rev. Phys. Chem.*, 61 (2010), pp. 129-148.

Djurišić, Aleksandra B. et al., "Optical Properties of ZnO Nanostructures", *Small*, 2, 8-9 (2006), pp. 944-961.

Dulub, Olga et al., "Novel Stabilization Mechanism on Polar Surfaces: ZnO(0001)-Zn", *Physical Review Letters*, 90, 1, 016102 (2003), pp. 1-4.

Erhart, Paul et al., "First-principles study of migration mechanisms and diffusion of oxygen in zinc oxide", *Physical Review B*, 73, 115207 (2006), pp. 1-9.

Goniakowski, Jacek et al., "Polarity of oxide surfaces and nanostructures", *Rep. Prog. Phys.*, 71, 016501 (2008), pp. 1-55.

Gorai, Prashun et al., "Electrostatic drift effects on near-surface defect distribution in $TiO_2$", *Applied Physics Letters*, 103, 141601 (2013), pp. 1-4; doi: 10.1063/1.4824614.

Gorai, Prashun et al., "Kinetics of oxygen interstitial injection and lattice exchange in rutile $TiO_2$", *Applied Physics Letters*, 104, 191602 (2014), pp. 1-4; doi: 10.1063/1.4876916.

Gorai, Prashun et al., "Kinetic model for electric-field induced point defect redistribution near semiconductor surfaces", *Applied Physics Letters*, 105, 021604 (2014), pp. 1-5; doi: 10.1063/1.4890472.

Gorai, Prashun et al., "Measurement of Defect-Mediated Oxygen Self-Diffusion in Metal Oxides", *ECS Journal of Solid State Science and Technology*, 1, 2 (2012), pp. Q21-Q24.

Gorai, Prashun et al., "Mechanism and kinetics of near-surface dopant pile-up during post-implant annealing", *Journal of Applied Physics*, 111, 094510 (2012), pp. 1-10; doi: 10.1063/1.4714556.

Gorai, Prashun et al., "Mechanism and energetics of O and $O_2$ adsorption on polar and non-polar ZnO surfaces", *The Journal of Chemical Physics*, 144, 184708 (2016), pp. 1-11; doi: 10.1063/1.4948939.

(Continued)

*Primary Examiner* — Haidung D Nguyen
(74) *Attorney, Agent, or Firm* — Brink Gilson & Lione

(57) ABSTRACT

A composition comprising an engineered defect concentration comprises a metal oxide single crystal having a polar surface and a bulk concentration of interstitial oxygen ($O_i$) of at least about $10^{14}$ atoms/cm$^3$. The polar surface comprises a concentration of impurity species of about 5% or less of a monolayer. A method of engineering a defect concentration in a single crystal comprises exposing a metal oxide single crystal having a polar surface to molecular oxygen at a temperature of about 850° C. or less, and injecting atomic oxygen into the single crystal at an effective diffusion rate $D_{\mathit{eff}}$ of at least about $10^{-16}$ cm$^2$/s.

10 Claims, 8 Drawing Sheets

(56) References Cited

OTHER PUBLICATIONS

Haneda, Hajime et al., "Oxygen Diffusion in Single- and Poly-Crystalline Zinc Oxides", *Journal of Electroceramics*, 4:S1 (1999), pp. 41-48.

Henkelman, Graeme et al., "A climbing image nudged elastic band method for finding saddle points and minimum energy paths", *The Journal of Chemical Physics*, 113, 22 (Dec. 8, 2000), pp. 9901-9904; doi: 10.1063/1.1329672.

Henkelman, Graeme et al., "Improved tangent estimate in the nudged elastic band method for finding minimum energy paths and saddle points", *The Journal of Chemical Physics*, 113, 22 (2000), pp. 9978-9985; doi: 10.1063/1.1323224.

Hoffman, J. W. et al., "Diffusion of Oxygen in Single Crystal Zinc Oxide", *Trans. Faraday Soc.*, 66 (1970), pp. 2346-2353.

Hollister, Alice G. et al., "Surface-based manipulation of point defects in rutile $TiO_2$", *Applied Physics Letters*, 102, 231601 (2013), pp. 1-5; doi: 10.1063/1.4810073.

Huang, Gui-Yang et al., "First-principles study of diffusion of oxygen vacancies and interstitials in ZnO", *Journal of Physics: Condensed Matter*, 21, 195403 (2009), pp. 1-6; doi: 10.1088/0953-8984/21/19/195403.

Ikeda, Jeri Ann S. et al., "Space Charge Segregation at Grain Boundaries in Titanium Dioxide: I, Relationship between Lattice Defect Chemistry and Space Charge Potential", *Journal of the American Ceramic Society*, 76, 10 (1993), pp. 2437-2446.

Janotti, Anderson et al., "Fundamentals of zinc oxide as a semiconductor", *Rep. Prog. Phys.*, 72, 126501 (2009), pp. 1-29; doi:10.1088/0034-4885/72/12/126501.

Jung, Michael Y. L. et al., "Effect of near-surface band bending on dopant profiles in ion-implanted silicon", *Journal of Applied Physics*, 95, 3 (2004), pp. 1134-1140; doi: 10.1063/1.1638621.

Kresse, Georg et al., "Competing stabilization mechanism for the polar ZnO(0001)-Zn surface", *Physical Review B*, 68, 245409 (2003), pp. 1-15; DOI: 10.1103/PhysRevB.68.245409.

Lauritsen, Jeppe V. et al., "Stabilization Principles for Polar Surfaces of ZnO", *ACS Nano*, 5, 7 (2011), pp. 5987-5994.

Moore, D. K. et al., "Oxygen diffusion in rutile from 750 to 1000 ° C. and 0.1 to 1000 MPa", *American Mineralogist*, 83 (1998), pp. 700-711.

Moore, W. J. et al., "II Diffusion of Zinc and Oxygen in Zinc Oxide", *Disc. Faraday Soc.*, 28 (1959), pp. 86-93.

Pangan-Okimoto, Kristine M. et al., "Model for Oxygen Interstitial Injection from the Rutile $TiO_2$(110) Surface into the Bulk", *The Journal of Physical Chemistry C*, 119 (2015), pp. 9955-9965; DOI: 10.1021/acs.jpcc.5b02009.

Robin, R. et al., "Application of a nondestructive single-spectrum proton activation technique to study oxygen diffusion in zinc oxide", *Journal of Applied Physics*, 44, 8 (1973), pp. 3770-3777; doi: 10.1063/1.1662839.

Sabioni, Antônio Claret Soares et al., "Oxygen Diffusion in Pure and Doped ZnO", *Materials Research*, 6, 2 (2003), pp. 173-178.

Seebauer, Edmund G. et al., "Control of Defect Concentrations within a Semiconductor through Adsorption", *Physical Review Letters*, 97, 055503 (2006), pp. 1-4.

Tasker, P. W., "The stability of ionic crystal surfaces", *J. Phys. C: Solid State Phys.*, 12 (1979), pp. 4977-4984.

Tomlins, Gregory W. et al., "Oxygen Diffusion in Single-Crystal Zinc Oxide", *Journal of the American Ceramic Society*, 81, 4 (1998), pp. 869-876.

Vaidyanathan, Ramakrishnan et al., "Measurement of Defect-Mediated Diffusion: The Case of Silicon Self-Diffusion", *AIChE Journal*, 52, 1 (2006), pp. 366-370.

Walch, Hermann et al., "Material- and Orientation-Dependent Reactivity for Heterogeneously Catalyzed Carbon—Bromine Bond Homolysis", *J. Phys. Chem. C*, 114 (2010), pp. 12604-12609.

Wang, Junpeng et al., "Oxygen Vacancy Induced Band-Gap Narrowing and Enhanced Visible Light Photocatalytic Activity of ZnO", *ACS Applied Materials & Interfaces*, 4 (2012), pp. 4024-4030; dx.doi.org/10.1021/am300835p.

Wang, Z. et al., "Estimating pre-exponential factors for desorption from semiconductors: consequences for a priori process modeling", *Applied Surface Science*, 181 (2001), pp. 111-120.

Zhang, Zhen et al., "Band Bending in Semiconductors: Chemical and Physical Consequences at Surfaces and Interfaces", *Chemical Reviews*, 112 (2012), pp. 5520-5551; dx.doi.org/10.1021/cr3000626.

Zheng, Hao et al.,"'Magic' Vicinal Zinc Oxide Surfaces", *Physical Review Letters*, 111, 086101 (2013), pp. 1-5.

* cited by examiner

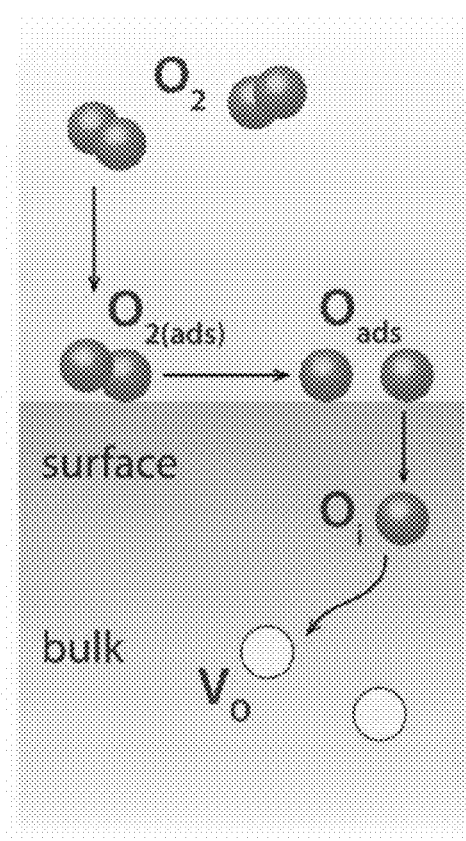
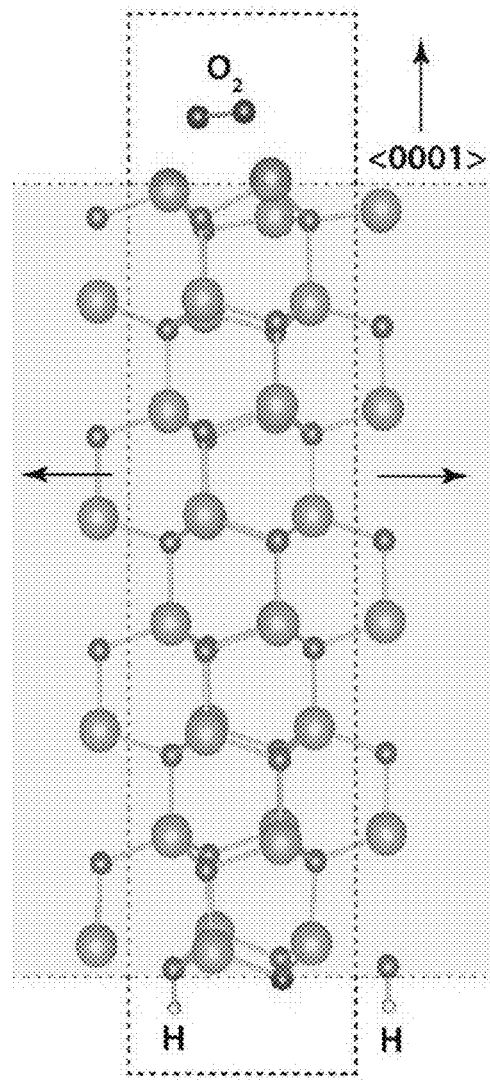
Figure 1
Figure 2

COMPOSITION COMPRISING AN ENGINEERED DEFECT CONCENTRATION

RELATED APPLICATION

The present patent document claims the benefit of priority under 35 U.S.C. § 119(e) to U.S. Provisional Patent Application Ser. No. 62/154,314, filed on Apr. 29, 2015, and hereby incorporated by reference in its entirety.

FEDERALLY FUNDED RESEARCH OR DEVELOPMENT

This invention was made with government support under contract number DMR1306822 awarded by the National Science Foundation. The U.S. government has certain rights in this invention.

TECHNICAL FIELD

The present disclosure is related generally to defect engineering and more specifically to controlling the species, concentration and/or spatial distribution of defects in metal oxides.

BACKGROUND

As a semiconductor, zinc oxide (ZnO) has a wide band gap (about 3.4 eV) and has attracted attention because of its potential applications in catalysis, as well as in optoelectronic devices, lasers, field effect transistors, and photovoltaic solar cells. The large-scale adoption of ZnO for these and other industrial applications hinges on obtaining atomic-scale control of surface and interface structure. It is known that the concentration and spatial distribution of point defects (e.g., vacancies, interstitial atoms and/or defect complexes) can strongly influence the manufacture and performance of ZnO and other metal oxides in various applications. For example, ZnO, which is an intrinsically O-deficient metal oxide, may contain large concentrations of oxygen vacancies ($V_o$) that are introduced during growth or post-growth treatments. Oxygen vacancies are undesirable in many photonic and electronic applications where they act as recombination centers, lowering UV band edge emissions and photocatalytic efficiencies, and contribute to charge compensation, hindering p-type doping in natively n-type oxides. Thus, methods to control oxygen vacancy concentration and distribution could be advantageous.

BRIEF SUMMARY

A composition comprising an engineered defect concentration comprises a metal oxide single crystal having a polar surface and a bulk concentration of interstitial oxygen ($O_i$) of at least about $10^{14}$ atoms/cm$^3$. The polar surface comprises a concentration of impurity species of about 5% or less of a monolayer.

A method of engineering a defect concentration in a single crystal comprises exposing a metal oxide single crystal having a polar surface to molecular oxygen at a temperature of about 850° C. or less, and injecting atomic oxygen into the single crystal at an effective diffusion rate $D_{eff}$ of at least about $10^{-16}$ cm$^2$/s.

BRIEF DESCRIPTION OF THE DRAWINGS

FIG. 1 is a schematic showing the adsorption of molecular oxygen on a polar surface of a metal oxide single crystal, followed by dissociation into injectable O adatoms that diffuse into the crystal as interstitial oxygen, annihilating oxygen vacancies.

FIG. 2 shows the hexagonal wurtzite structure of zinc oxide (ZnO).

DETAILED DESCRIPTION

Figures 3A, 3B, 3C:
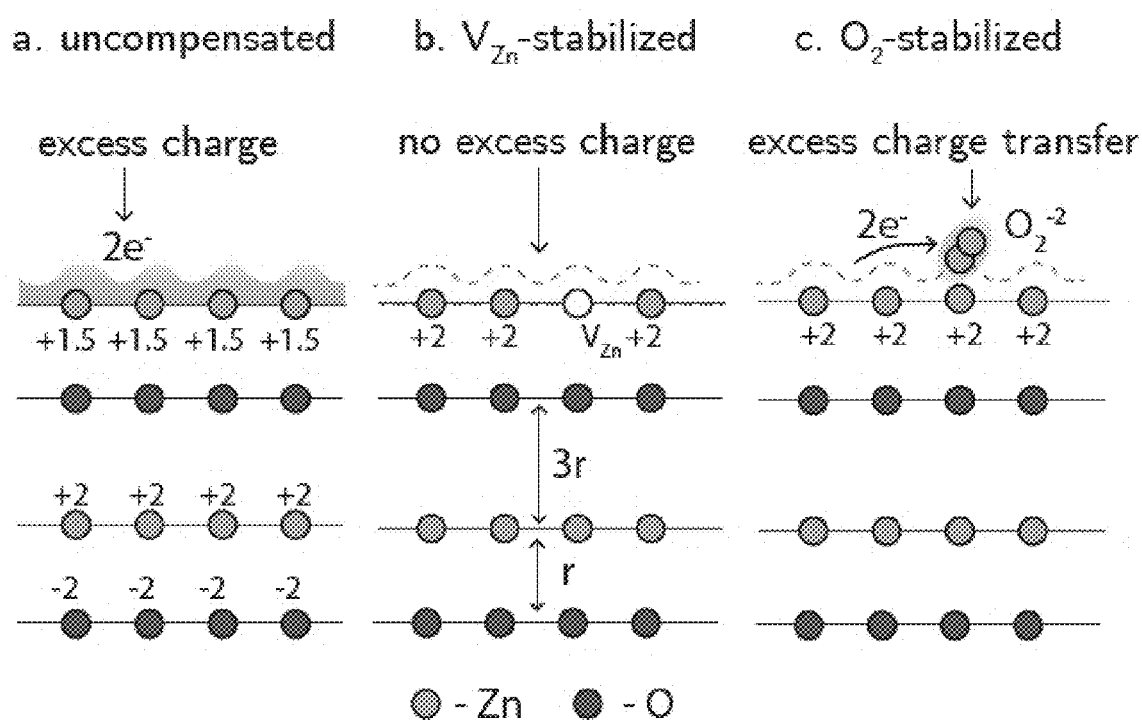
FIG. 3A shows schematically the excess charge associated with a polar surface (0001) of ZnO.
FIG. 3B shows schematically stabilization of the ZnO (0001) polar surface by zinc vacancies, where excess electrons are removed from the surface.
FIG. 3C shows schematically stabilization of the ZnO (0001) polar surface by molecular oxygen, where excess electrons are transferred to $O_2$, returning Zn ions to a +2 state.

The adsorption and ensuing dissociation of $O_2$ onto polar metal oxide surfaces, followed by the injection of surface O adatoms into the interior of the metal oxide crystal, has been found to be a key approach for defect engineering to obtain compositional control over the near-surface region of metal oxides such as zinc oxide (ZnO). Thus, a method of engineering a defect concentration in a metal oxide single crystal is set forth herein. Also presented is a composition comprising an engineered defect concentration, as well as functional devices that may include such a composition.

A composition having an engineered defect concentration comprises a metal oxide single crystal having a polar surface and a bulk concentration of interstitial oxygen ($O_i$) of at least about $10^{14}$ atoms/cm$^3$. The polar surface is atomically clean and has a concentration of impurity species of about 5% or less of a monolayer (about 0.05 ML or less) or about 1% or less of a monolayer (about 0.01 ML or less). It should be understood that the concentration of impurity species being referred to is a surface concentration as opposed to a bulk concentration, which is why the impurity species concentration is described in terms of a percentage of a monolayer.

As used herein, a polar surface is one that comprises excess surface charge due to the presence of a plane of metal cations or oxygen anions having a lower coordination than in the bulk. The metal oxide single crystal may have a wurtzite, zincblende, rocksalt, perovskite, trigonal, cubic spinel, or other crystallographic lattice structure that is geometrically capable of yielding a polar surface. The polar surface may be attained by cutting or cleaving the single crystal between alternating planes of cations and anions.

Polar surfaces are electrostatically driven toward stabilization. In the present work, the adsorption of molecular oxygen ($O_2$) is exploited to stabilize polar surfaces. In an oxygen-rich environment at suitable temperatures, molecular oxygen may be adsorbed onto a polar surface and can dissociate into injectable O adatoms, as shown schematically in FIG. 1. These O atoms can diffuse into the crystal as interstitial oxygen ($O_i$) and annihilate less desirable oxygen vacancies ($V_o$) throughout the crystal, leaving interstitial oxygen as the majority defect. This approach leads to substantial increases in oxygen diffusivity compared to $V_o$-mediated diffusion and to unprecedented oxygen interstitial concentrations [$O_i$]. The determination of [$O_i$] based on diffusivity data is explained in detail below.

The interstitial oxygen may be isolated and/or may form complexes with other mobile defects. For example, $O_i$ may form a complex with interstitial M or M vacancies, where M is taken to represent the metal(s) present in the metal oxide. In one example, the metal oxide single crystal may comprise zinc oxide (ZnO), where Zn is M, and where the crystal comprises a zincblende or wurtzite structure. In other examples, the metal oxide single crystal may comprise NiO (e.g., having the rock salt crystal structure), lithium cobaltite LiCoO$_2$ (e.g., having a trigonal or cubic spinel crystal structure) or a perovskite such as KTaO$_3$ or SrTiO$_3$.

ZnO is an ionic material that most commonly has a hexagonal wurtzite structure, as illustrated in FIG. 2. A ZnO single crystal comprises alternating planes of Zn$^{+2}$ cations and O$^{-2}$ anions along the c-axis or <0001> direction. When cleaved perpendicular to the c-axis, a ZnO crystal has two polar surfaces: a Zn-terminated (0001) surface and an O-terminated (000$\bar{1}$) surface. The polar nature of the surfaces may be attributed to the bonding network: the as-cleaved (0001) surface exposes Zn atoms that are three-fold coordinated, in contrast to the four-fold coordination in the bulk of the crystal. As each surface Zn atom has only ¾ of its bonds present, it can transfer only 1.5 electrons rather than 2 electrons to neighboring O atoms. Consequently, the surface layer possesses an excess surface charge of ½ electron per Zn atom (or two electrons per four Zn atoms), as shown schematically in FIG. 3A.

The excess surface charge characteristic of a polar surface can be removed to stabilize the surface by oxygen adsorption, as described here, and/or by reconstruction, faceting or surface vacancy formation. For example, considerations of electron counting rules show that formation of 0.25 monolayer (ML) neutral $V_{Zn}$ (as illustrated schematically in FIG. 3B) is sufficient in principle to remove the excess charge from a Zn-terminated (0001) polar surface. Analogous mechanisms exist for the O-terminated (000$\bar{1}$) polar surface, where 2 electrons per 4 surface O atoms are added instead of withdrawn for stabilization. The $O_2$ molecule is an electron scavenger that can extract up to two electrons to become a peroxo radical ($O_2^{-2}$), as illustrated schematically in FIG. 3C. Full electrostatic stabilization of the (0001) surface may be achieved in principle by adsorbing one $O_2$ molecule for every four Zn atoms (equivalent to 0.25 ML $O_2$), or by combinations of $O_2$ adsorbates with other stabilizing species totaling 0.25 ML.

Quantum calculations indicate that oxygen plays a role in stabilizing a polar surface, not only by direct participation in fulfilling electron counting rules as described above, but also indirectly, where $O_2$ in the gas phase provides a thermodynamic environment whose chemical potential favors surface reconstructions having geometries amenable to O or $O_2$ adsorption. The details of this indirect thermodynamic effect may vary from material to material and also among crystallographic orientations of a given material. The quantum calculations also demonstrate that O or $O_2$ can in fact—and not just in principle—adsorb on the polar surface.

Figure 4A:
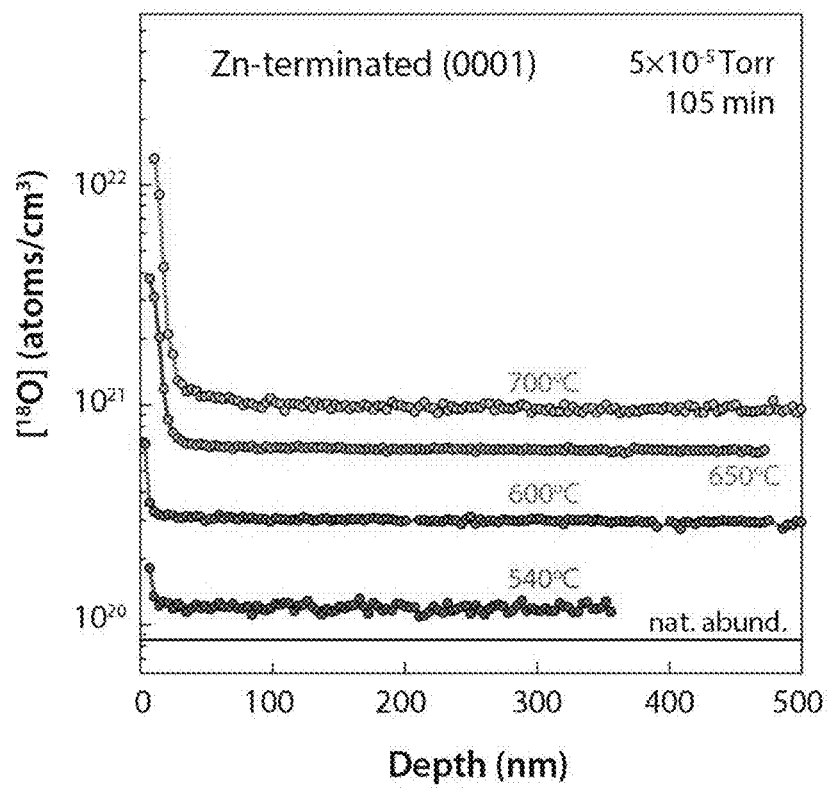
FIG. 4A shows isotopic oxygen ($^{18}$O) diffusion profiles in ZnO with a Zn-terminated (0001) surface subsequent to annealing (540° C., 600° C., 650° C., 700° C.) in $^{18}O_2$ gas at $5\times10^{-5}$ Torr. The exponential profile shapes in the deep bulk (which appear linear on a semi-logarithmic scale) suggest diffusion via a highly mobile intermediate species.
Figure 4B:
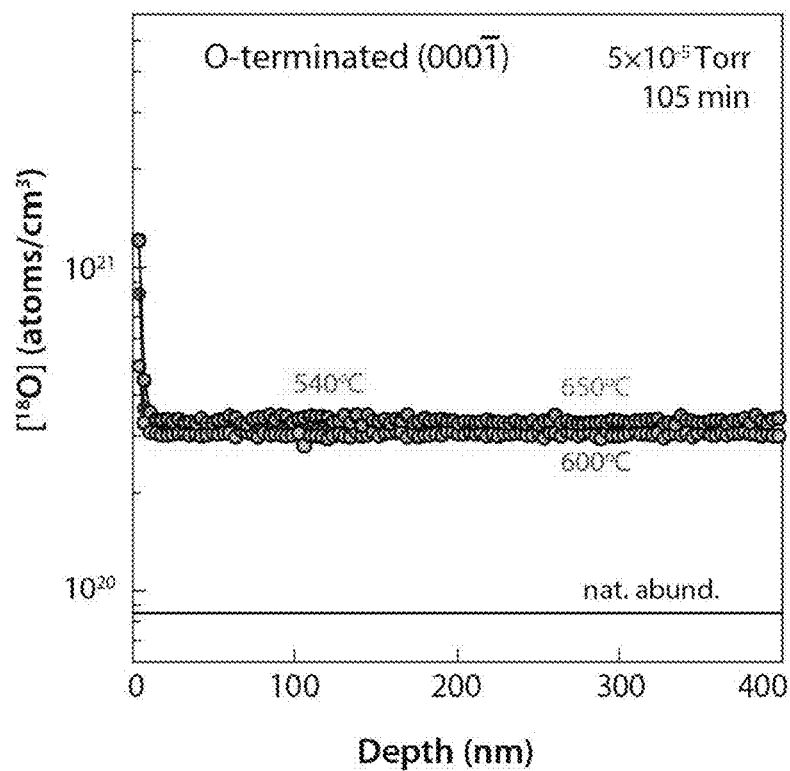
FIG. 4B shows isotopic oxygen ($^{18}$O) diffusion profiles in ZnO with an O-terminated (000$\bar{1}$) surface subsequent to annealing (540° C., 600° C., 650° C., 700° C.) in $^{18}O_2$ gas at $5\times10^{-5}$ Torr. As in FIG. 4A, the exponential profile shapes in the deep bulk (which appear linear on a semi-logarithmic scale) suggest diffusion via a highly mobile intermediate species.

Isotopic oxygen self-diffusion experiments confirm the creation of a mobile oxygen defect, which is believed to be interstitial oxygen, at the polar surfaces of ZnO, (0001) and (000$\bar{1}$), when the crystal is exposed to suitable temperatures and oxygen conditions, as described in this disclosure. FIGS. 4A and 4B show diffusion profiles of $^{18}$O for the Zn-terminated (0001) and O-terminated (000$\bar{1}$) surfaces, respectively, in the temperature range of 540° C.–700° C. when exposed to an oxygen pressure of 5×10$^{-5}$ Torr.

The diffusion experiments reveal that extremely high values of diffusivity $D_{eff}$ may be achieved for mobile oxygen defects in the metal oxide single crystal due in significant part to the polarity and low impurity levels of the exposed crystal surfaces. The polarity drives the need for stabilization, which may be achieved through oxygen adsorption as explained above, and the surface cleanliness ensures that surface binding sites (or surface active sites) are available to accommodate the adsorbed oxygen. At a given temperature, the diffusion rate depends not only on the mobility of the defect but also on the number of defects. The rate of defect exchanges that occur at a given temperature is dependent on defect formation and annihilation at the surface, which in turn is influenced by the availability of surface active sites. As indicated above, the polar surface is atomically clean with a concentration of impurity species that may be 0.01 ML or less. In some cases, the concentration of impurity species may be about 0.005 ML or less, or as low as about 0.001 ML (about 0.1% of a monolayer). One way to achieve this level of surface cleanliness is to carry out the diffusion experiments in a high vacuum or an ultrahigh vacuum environment (e.g., background pressure of 1×10$^{-8}$ Torr or better for reactive gases), as described further below.

Figure 10:
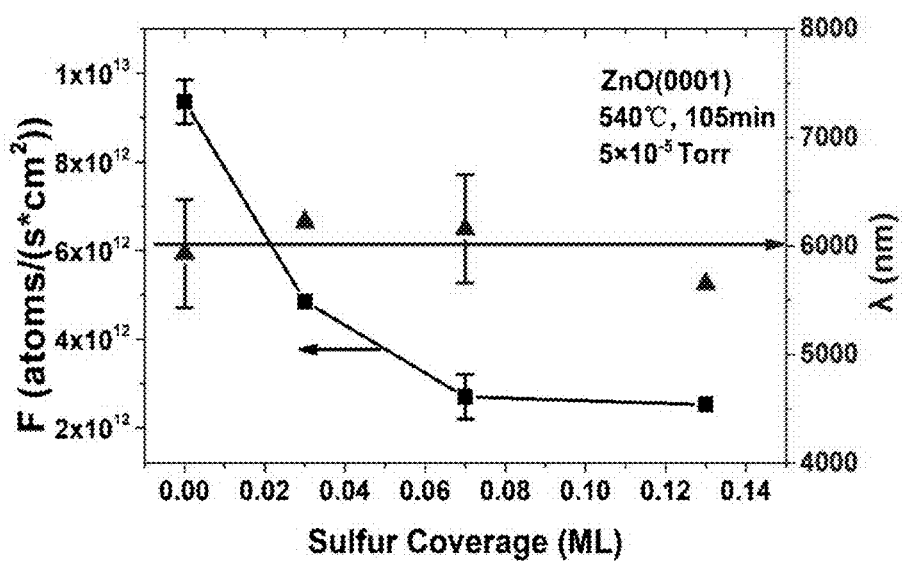
FIG. 10 shows how low levels of adsorbed sulfur on the Zn-terminated (0001) surface of a ZnO single crystal impact the defect injection flux (F) of injected O interstitials.
Figure 11:
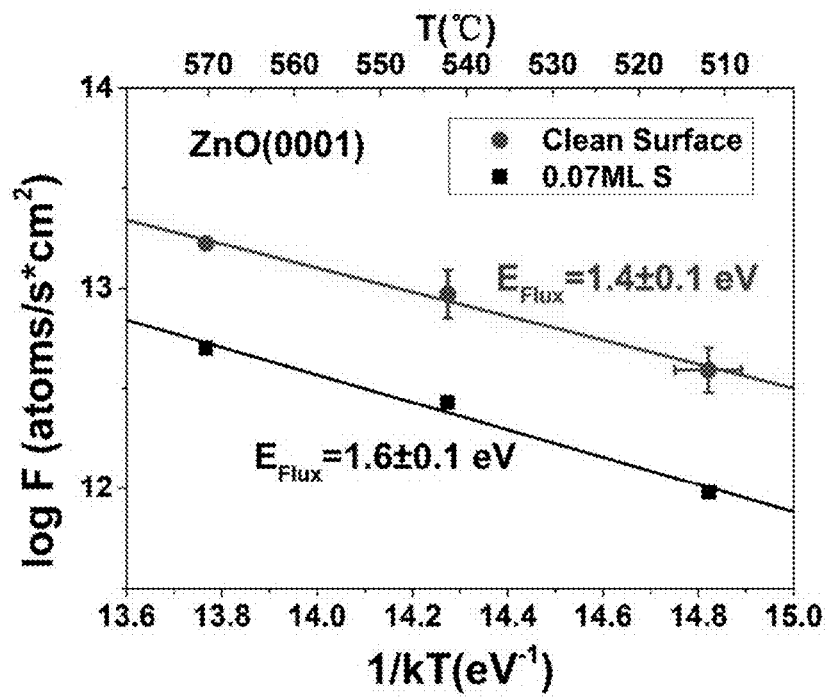
FIG. 11 shows the defect injection flux as a function of 1/kT for a clean Zn-terminated (0001) surface compared to a Zn-terminated (0001) surface that includes 7% of a monolayer of sulfur.

Diffusion experiments carried out on single crystal ZnO with low levels of adsorbed sulfur on the Zn-terminated (0001) surface show the impact of surface impurity levels on the diffusion rate of O interstitials. Referring to FIG. 10, the response of the defect injection flux (F) of injected O interstitials to the presence of the sulfur is measured. The injection flux drops by a factor of more than 2 in the presence of 3% of a monolayer of sulfur, and by a factor of 3 in the presence of 7% of a monolayer of sulfur. FIG. 11 shows the defect injection flux as a function of 1/kT for a clean Zn-terminated (0001) surface compared to a Zn-terminated (0001) surface that includes 7% of a monolayer of sulfur. The results indicate that the activation energy for interstitial injection as given by the slopes of the lines is essentially invariant (near 1.5 eV) as a function of sulfur concentration. The decrease in F due to sulfur therefore results entirely from a corresponding pre-exponential factor for injection. This behavior is fully consistent with a standard site-blocking mechanism, in which sulfur simply poisons the injection sites for oxygen interstitial injection. Since sulfur is from the same column of the Periodic Table as oxygen and is chemically similar in many ways, substitution of sulfur for surface oxygen could be reasonably expected to have a less significant effect than many other possible elements. Yet, as evidenced by the data of FIGS. 10 and 11, the effect of even sulfur is notably large.

The high values measured for oxygen diffusivity $D_{eff}$ are consistent with high concentrations of interstitial oxygen. When exposed to oxygen-rich conditions at relatively low temperatures, e.g., below 850° C., a ZnO single crystal may exhibit a diffusivity $D_{eff}$ of at least about $10^{-16}$ cm$^2$/s, at least about $10^{-15}$ cm$^2$/s, at least about $10^{-14}$ cm$^2$/s, at least about $10^{-13}$ cm$^2$/s, or at least about $10^{-12}$ cm$^2$/s. The temperature to which the polar surface is exposed may be about 800° C. or less, about 750° C. or less, or about 700° C. or less, and the diffusivity $D_{eff}$ may be as high as about $10^{-11}$ cm$^2$/s or as high as about $10^{-10}$ cm$^2$/s. These values are up to six orders of magnitude higher than oxygen defect diffusivities obtained from ZnO samples in the prior art. As will be discussed in further detail, the magnitude of the diffusivity may depend on the temperature and the surface polarity (e.g., whether the surface is cation- or anion-terminated). Typically, the temperature is at least about 300° C., or at least about 500° C., to achieve the desired diffusion rate.

A striking difference between the diffusion profiles of the Zn-terminated and O-terminated samples is in their temperature dependence. Profile shifts with temperature are observed for the Zn-terminated surface (as can be seen in FIG. 4A) but temperature has a negligible effect on the diffusion profiles for the O-terminated surface, at least in the range probed in this study (as shown in FIG. 4B). Naked eye inspection reveals that the Zn-terminated crystals lose their yellowish tinge after annealing, and the crystals become more colorless. In contrast, the O-terminated samples partially retain their yellowish tinge after annealing.

The yellowish tinge of ZnO crystals before or after annealing may be attributed to oxygen vacancies. The more saturated the yellowish hue, the larger the concentration of $V_O$. The loss of the yellowish tinge upon annealing can be directly related to the annihilation of oxygen vacancies via adsorption of molecular oxygen followed by dissociation and injection of $O_i$. In oxides, $O_i$ spontaneously recombines with $V_O$. The O-terminated samples show less pronounced color loss which is believe to be related to a smaller amount of mobile oxygen defect injection into the bulk from the (000$\bar{1}$) surface. It is also possible that $V_O$ from the bulk may migrate to the surface and be annihilated by surface adsorbed oxygen, leading to loss of the yellowish tinge. However, it is believed that the temperatures employed in this investigation are far too low to mobilize $V_O$ to migrate to the surface.

The diffusion profiles have two distinct regimes: (1) a near-surface region (~5-35 nm) showing accumulation (or pile-up) of isotopic oxygen, and (2) deeper profile extensions into the bulk. The amount of near-surface pile-up is found to increase with temperature for the Zn-terminated surface but remains almost constant with temperature for the O-terminated surface. The pile-up may have an electrostatic origin, as discussed further below. Unlike oxygen self-diffusion in rutile TiO$_2$, which was investigated in U.S. Pat. No. 8,871,670 (issued Oct. 28, 2014 to Seebauer and hereby incorporated by reference in its entirety), the diffusion tails in ZnO are more gradually sloping, which indicates that the mean diffusion lengths are on the order of a few microns.

The bulk diffusion profiles exhibit exponential tails, which manifest as straight lines on the semilogarithmic scale of FIGS. 4A and 4B. Exponential diffusion tails are a signature of a highly mobile defect species that mediates diffusion, in this case a mobile oxygen defect which is believed to include interstitial oxygen. Oxygen diffusion mediated by oxygen vacancies typically results in diffusion profiles that have a complementary error function shape, rather than the exponential shape observed here.

Figure 12:
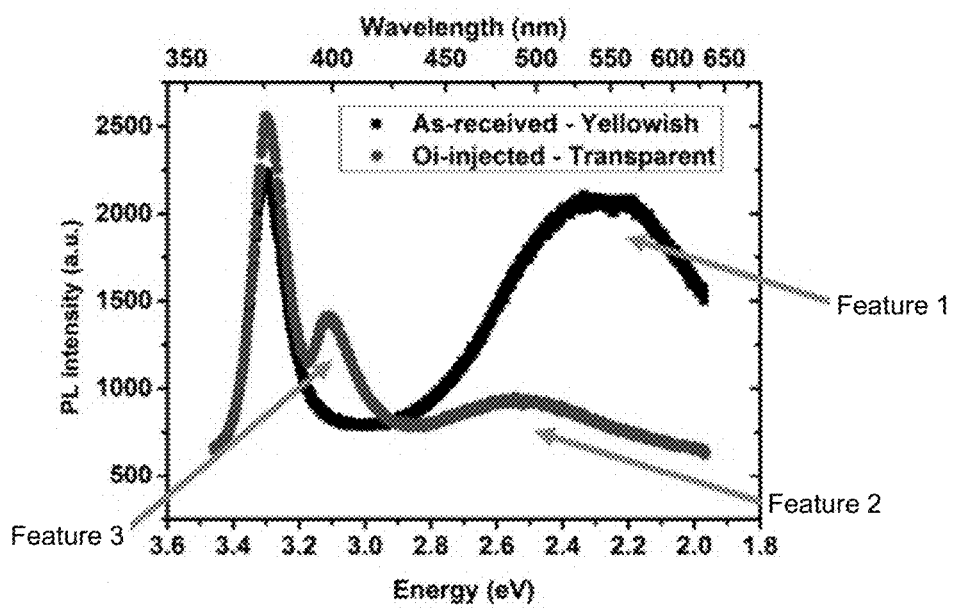
FIG. 12 shows photoluminescence data from two samples of Zn-terminated ZnO (0001): (1) as-received from the manufacturer, and (2) after annealing in oxygen.

In addition, optical photoluminescence data show how defect concentrations can be controlled as a function of process conditions. Referring to FIG. 12, the photoluminescence data are from two samples of Zn-terminated ZnO (0001): (1) as-received from the manufacturer, and (2) after annealing in oxygen as described elsewhere in this disclosure (with no sulfur). The data for the as-received sample, which is visibly yellowish, include two main peaks: one at 3.33 eV or 375 nm and another at 2.3 eV or 550 nm (labeled as "Feature 1"). The peak at 3.33 eV (375 nm) is from the band gap of ZnO and is not defect related, while Feature 1 at 2.3 eV (550 nm) represents the well-known green emission from ZnO that is of much interest in optoelectronic devices. It is believed that emission at 550 nm can signify the presence of oxygen vacancies. It is noted that there is some controversy in the scientific literature about which defects are responsible for which photoluminescence peaks, especially at wavelengths far from the band gap emission. Broad peaks may in some cases represent a composite from more than one kind of defect.

For the annealed ($O_i$-injected) sample that is colorless, there are two peaks in addition to the band-gap peak at 3.33 eV; one of the peaks is at 2.5 eV or 480 nm (labeled as "Feature 2"), and the other is at 3.1 eV or 400 nm (labeled as "Feature 3"). The peak at 2.5 eV (480 nm) may be attributed to residual lithium contamination that is common in ZnO crystals. Feature 3 at 3.1 eV (400 nm) is believed to be an entirely new peak that may be due interstitial defects. The scientific literature identifies a Zn interstitial energy level that is 0.22 eV below the conduction band, which could lead to such emission.

Figure 13:
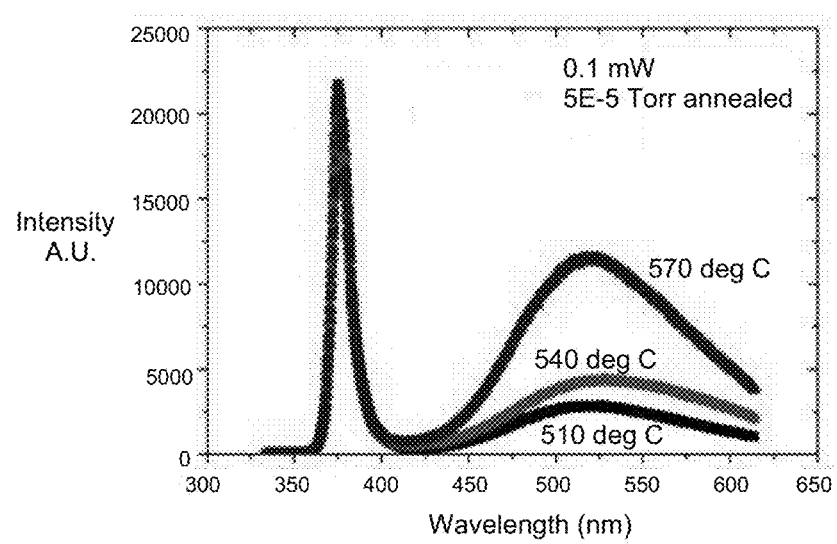
FIG. 13 shows photoluminescence data for Zn-terminated ZnO (0001) obtained after annealing in oxygen at different annealing temperatures.

FIG. 13 includes photoluminescence data for Zn-terminated ZnO (0001) taken after a set of annealing experiments carried out as described above but at different annealing temperatures. The peak near 520 nm (2.4 eV) moves around a bit, which suggests that it may be a composite having contributions from more than one type of defect. Clearly, however, the peak grows in intensity with increasing temperature. It is postulated in the scientific literature that a peak at 2.35 eV may be associated with zinc vacancies and further that the concentration of O interstitials may increase in parallel with the concentration of zinc vacancies under O-rich conditions. Thus, the growth of the peak shown here as a function of temperature may be indicative of an increase in concentration of O interstitials in the zinc oxide single crystal. In aggregate, the photoluminescence data indicate that the surface treatment employed can modify the populations of several kinds of defects in substantial ways that are readily observable by noninvasive spectroscopic means.

Based on the findings described herein, a method of engineering a defect concentration in a metal oxide single crystal is described. The method entails exposing a single crystal comprising a polar surface to molecular oxygen at a temperature of about 850° C. or less, and injecting atomic oxygen into the single crystal as interstitial oxygen at an effective diffusion rate or diffusivity $D_{eff}$ of at least about $10^{-14}$ cm$^2$/s. As described above, injecting atomic oxygen into the single crystal may comprise adsorbing a portion of the molecular oxygen onto the polar surface, and the molecular oxygen on the polar surface may then dissociate to form the atomic oxygen. As shown schematically in FIG. 1, the atomic oxygen may then diffuse into the crystal as interstitial oxygen.

The diffusion data establish that extremely high diffusion rates may be attained for the mobile oxygen species. The effective oxygen diffusivity $D_{eff}$ may be at least about $10^{-16}$ cm$^2$/s, at least about $10^{-15}$ cm$^2$/s, at least about $10^{-14}$ cm$^2$/s, at least about $10^{-13}$ cm$^2$/s, or at least about $10^{-12}$ cm$^2$/s, and $D_{eff}$ may be as high as about $10^{-11}$ cm$^2$/s or as high as about $10^{-10}$ cm$^2$/s. In some cases, the temperature to which the polar surface is exposed may be about 800° C. or less, about 750° C. or less, or about 700° C. or less. Typically, the temperature is at least about 300° C., or at least about 500° C. The metal oxide single crystal may be exposed to the molecular oxygen at an oxygen pressure ($P_{O2}$) in the range of $10^{-7}$ Torr to 760 Torr (atmospheric pressure). In some cases, the oxygen pressure may be in the range of $10^{-6}$ Torr to $10^{-2}$ Torr, or from $10^{-5}$ to $10^{-4}$ Torr. The exposure to the molecular oxygen may occur for a time duration of from about 1 minute to about 120 minutes, or from about 10 minutes to about 90 minutes.

To promote surface cleanliness, the method may be carried out in a high vacuum or an ultrahigh vacuum (UHV) environment (e.g., a sealed vacuum chamber under active pumping by one or more pumps, such as turbomolecular pumps, ion pumps and/or cryopumps). Thus, prior to introduction of the molecular oxygen, a base or background pressure of reactive gases of $5 \times 10^{-8}$ Torr or lower may be achieved in the environment. In some cases, the background pressure may be about $1 \times 10^{-8}$ Torr or lower. The metal oxide single crystal may be loaded into the ultrahigh vacuum environment for some time duration (e.g., at least 8 hours) prior to the exposure to molecular oxygen. Accordingly, the polar surface may be atomically clean and have a concentration of impurity species of about 5% or less of a monolayer (0.05 ML or less). As described above, the concentration of impurity species may also be 0.01 ML or less, and in some cases the concentration of impurity species may be about 0.005 ML or less, or as low as about 0.001 ML (about 0.1% of a monolayer). The metal oxide single crystal may be zinc oxide or another oxide having any of the characteristics described above. The polar surface may be cation-terminated or anion-terminated.

Figure 5:
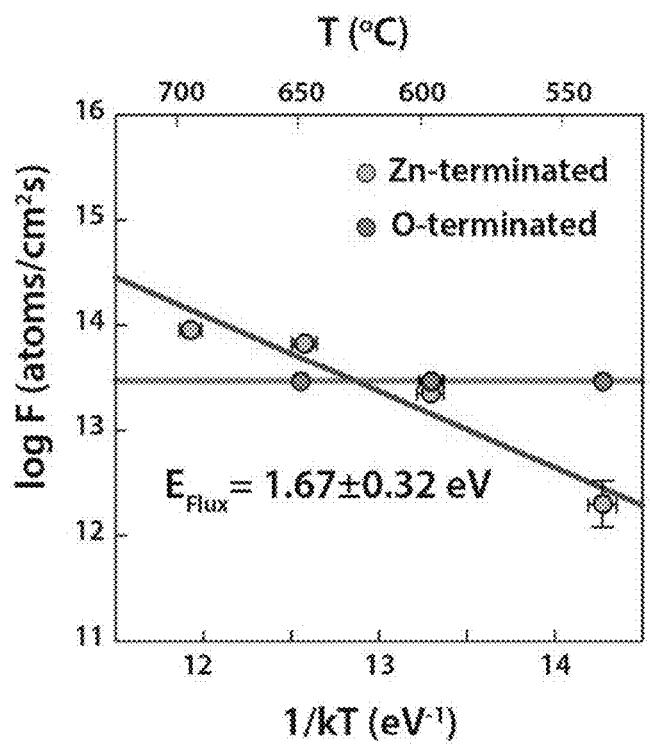
FIG. 5 is a plot showing the temperature dependence of the net defect injection flux (F) for Zn- and O-terminated surfaces at $5\times10^{-5}$ Torr ($P_{O2}$).

It has been found that the net injection flux of the mobile oxygen defects is highly sensitive to the polar surface orientation, that is, whether the polar surface is cation-terminated or anion-terminated. In the examples discussed herein with ZnO polar surfaces, it is found that $O_2$ adsorbs most readily on the Zn-terminated polar surface, and under some conditions on the O-terminated polar surface. In contrast, $O_2$ adsorption does not occur readily at all on nonpolar surfaces. Referring to the data of FIG. 5, it can be seen that the injection rate at a Zn-terminated (0001) ZnO surface may be controlled as a function of temperature, while the injection rate at the O-terminated (000$\bar{1}$) ZnO surface is substantially temperature-independent.

To quantify the defect injection flux (F; shown in FIG. 5), the mean diffusion length of the mobile intermediate before immobilization ($\lambda$) and the effective diffusivity ($D_{eff}$), the exponential diffusion profiles were fitted with an analytical mathematical model that accounts for injection, diffusion, and lattice exchange of the mobile defect. The solution of the governing diffusion equations is given by, $$\ln\left(\frac{C_S - C_{S0}}{C_{S0}^T - C_{S0}}\right) = \ln\left(\frac{F}{\lambda[C_{S0}^T - C_{S0}]}t\right) - \frac{x}{\lambda} \quad (1)$$

where $C_s$ is the measured concentration of $^{18}$O, $C_{S0}$ is the natural abundance concentration of $^{18}$O ($8.5 \times 10^{19}$ cm$^{-3}$) in the crystal, $C^T_{S0}$ denotes the total concentration of the lattice sites ($4.1 \times 10^{22}$ cm$^{-3}$) capable of exhanging with the mobile defect, t is the diffusion time and x is the spatial coordinate with x=0 referring to the surface. Eq. (1) applies in the short-time limit when kick-out of $^{18}$O from the lattice site is negligible. Fitting Eq. (1) to measured exponential diffusion profiles yields the value of $\lambda$ from the slope of the straight line and F from the y-axis intercept. The effective diffusivity ($D_{eff}$) can then be calculated from F and $\lambda$ as:

$$D_{eff} = \frac{F\lambda}{(C_{S0}^T - C_{S0})} \quad (2)$$

While F depends upon conditions at the surface, $\lambda$ depends upon only bulk parameters.

Figure 6:
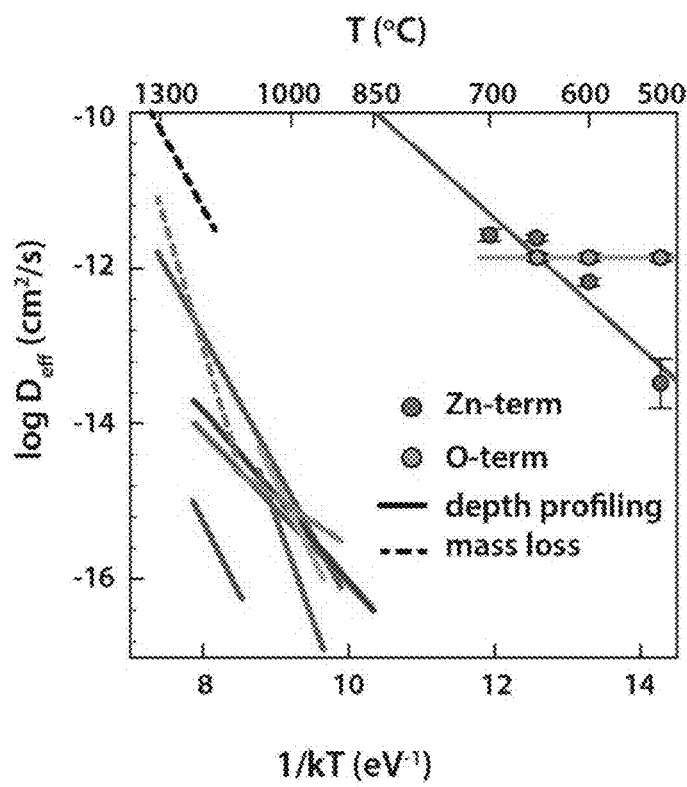
FIG. 6 is a plot showing $D_{eff}$ for oxygen self-diffusion for the Zn- and O-terminated ZnO samples (right hand side of plot) compared to values obtained from ZnO at higher temperatures in the prior art (left hand side of plot).

The present experiments yield an activation energy of 1.92±0.46 eV for the Zn-terminated surface. The measured pre-exponential factor of $10^{-1.34\pm2.60}$ cm$^2$/s combined with the lower activation energy results in oxygen self-diffusivities that are six or more orders of magnitude larger than those reported in the literature below 850° C., with the difference narrowing somewhat at higher temperatures. As noted above, the substantially larger diffusivities are an indication that a highly mobile O defect, such as interstitial O, mediates O diffusion. The O-terminated (000$\bar{1}$) surface is a peculiar case where $D_{eff}$ is temperature independent. However, $D_{eff}$ is similar in magnitude to the Zn-terminated surface and still substantially larger than previously reported data, as can be seen in FIG. 6.

The data for $D_{eff}$ can be used to obtain values of interstitial oxygen concentration [$O_i$] by the procedure described below. The following material properties are used in the equations, assuming the metal oxide single crystal is ZnO having a hexagonal (zincite) structure: Density=5.61 g/cm$^3$, formula weight=81.41 g/mol, where the density of O atoms in the lattice [$O_{lattice}$] is $4.15 \times 10^{22}$ cm$^{-3}$. The melting temperature $T_{melt}$ is 2250 K, and the heat of fusion $\Delta H_{melt}$ is 230 J/g=0.194 eV.

The interstitial oxygen concentration [$O_i$] may be determined as follows from the effective diffusivity $D_{eff}$. At equilibrium, $D_{eff} = D_{hop} \times [O_i]/[O_{lattice}]$, as discussed in C. Zener, J. Appl. Phys., 22 (1951) 372. $D_{eff}$ may be determined from the data of FIG. 6 for a given temperature. The site-to-site hopping diffusivity $D_{hop}$ is not known directly, but may be estimated as follows: $D_{hop} = D_{0,hop} \exp(-E_{hop}/k_B T)$, where the pre-exponential factor $D_{0,hop} = \nu L^2 \exp(\Delta S_{hop}/k_B)$. The vibration frequency $\nu$ is about $k_B T/h$, and the jump length L can be taken to be equal to $[O_{lattice}]^{1/3}$.

The entropy of hopping can be estimated by $\Delta S_{hop} \approx \Delta H_{melt}/T_{melt}$, also as reported by Zener in the above-mentioned reference. The hopping activation energy $E_{hop}$ is not known directly; however, it is likely to be close to $E_{hop}$ for interstitial defects in other semiconductors, such as Si (0.72 eV) and TiO$_2$ (0.65 eV). Thus, a reasonable assumption for $E_{hop}$ for ZnO is 0.7 eV. Thus, $[O_i]=[O_{lattice}]D_{eff}/D_{hop}$. Note how $[O_i]$ is proportional to $D_{eff}$.

On this basis, depending on the temperature and value of $D_{eff}$, the interstitial oxygen concentration $[O_i]$ can be calculated to be in the range of about $10^{14}$ atoms/cm$^3$ to $10^{17}$ atoms/cm$^3$. For example, $[O_i]$ may be at least about $1\times10^{14}$ atoms/cm$^3$, at least about $3\times10^{14}$ atoms/cm$^3$, at least about $1\times10^{15}$ atoms/cm$^3$, or at least about $1\times10^{16}$ atoms/cm$^3$. $[O_i]$ may also be up to about $1\times10^{17}$ atoms/cm$^3$ or up to about $3\times10^{17}$ atoms/cm$^3$.

The distribution of oxygen defects and dopants near surfaces (and interfaces) of oxide semiconductors can influence the efficiency of solar cells, sensors and other devices. In nanostructured materials, the bulk lies close to the surface, typically within a few tens of nanometers to a few hundreds of nanometers. At small length scales, the high surface to volume ratios may result in a strong surface to bulk coupling. It should be noted that the metal oxide single crystal may have at least one linear dimension of about 100 nm or less and may thus be described as nanostructured. A single crystal having one linear dimension of about 100 nm or less may be described as a thin film; a single crystal having two linear dimensions of about 100 nm or less may be described as a nanorod, nanowire or nanotube; and a single crystal having three linear dimensions of about 100 nm or less may be described as a nanoparticle. It is also contemplated that the metal oxide single crystal may include a dopant. For example, zinc oxide may be doped with an element such as Al, As, Fe, Ga, Mg, N, P, Sb and/or Y. The dopant may be introduced to the metal oxide single crystal before or after the mobile oxygen defects are injected.

Figure 7:
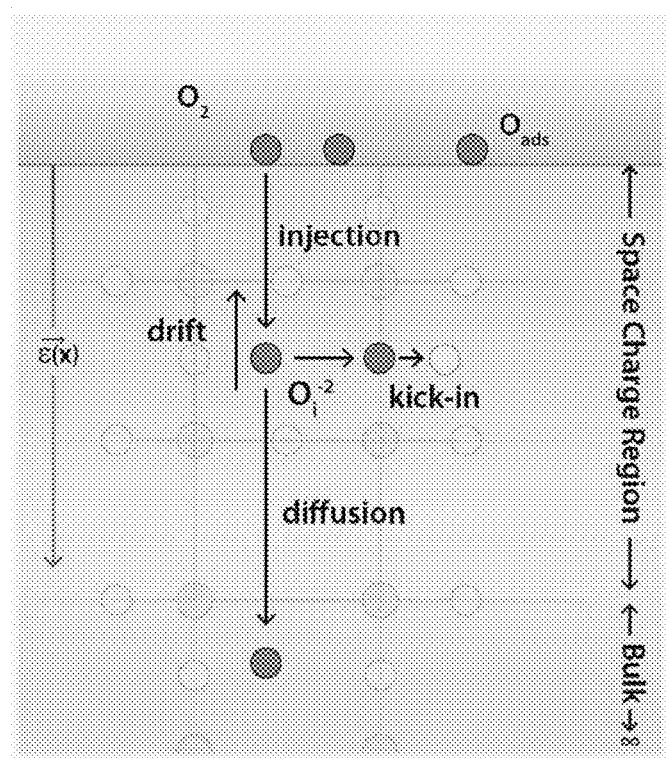
FIG. 7 schematically shows the influence of an electric field near the polar surface on diffusion of injected oxygen.
Figure 8:
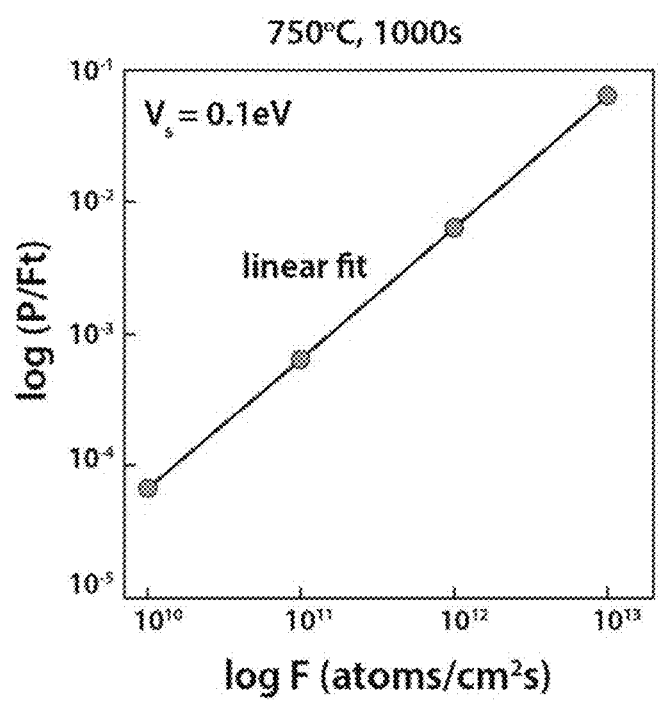
FIG. 8 is a plot of log (P/Ft) versus log F as determined by an analytical model, where P represents pile-up, F represents net defect injection flux, and t represents time. The plot shows the linear relationship between P and F.
Figure 9:
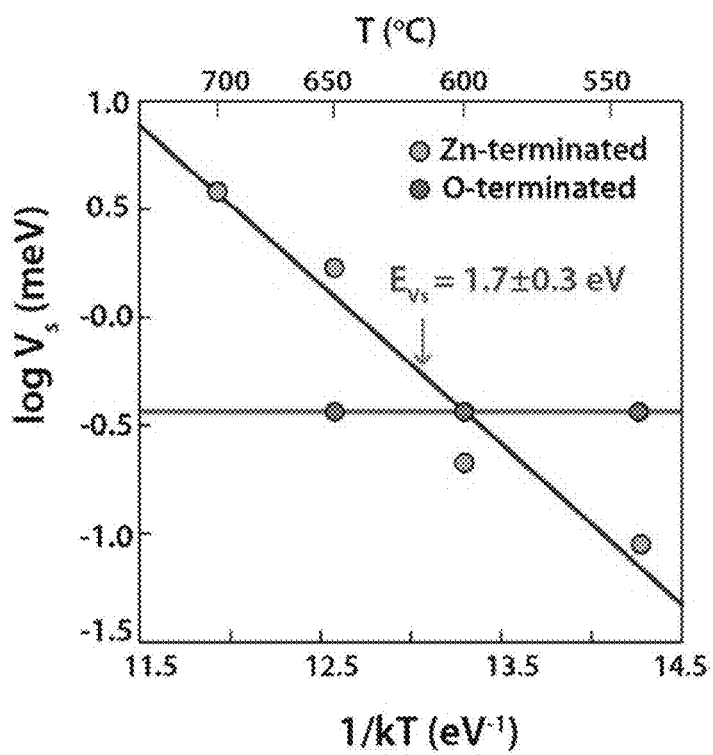
FIG. 9 shows Arrhenius temperature dependence of the surface potential ($V_s$) for the Zn-terminated ZnO and O-terminated ZnO at $5\times10^{-5}$ Torr. The activation energy for buildup of the surface potential with temperature is approximately 1.7 eV for the Zn-terminated surface, while the surface potential remains almost constant at the O-terminated surface.

The surface to bulk coupling referred to above may have an electrostatic origin where charged bulk defects interact with electric fields in the space charge layers near the semiconductor surface. FIG. 7 schematically depicts this electrostatic mechanism. Under appropriate surface conditions, oxygen from the surface is injected into the bulk of the oxide semiconductor as charged oxygen interstitials ($O_i^{-2}$) via an active site mechanism, as described above. For downward band bending in the space charge region of a natively n-type material, such as ZnO, the near-surface electric field $\vec{\varepsilon}(x)$ points into the bulk. The field-induced drift of the $O_i^{-2}$ injected from the surface opposes the diffusional motion into the bulk, increasing the residence time in the space charge region. The prolonged stay in the space charge regions increases the opportunity for exchange of $O_i^{-2}$ with the lattice O via kick-in, resulting in pile-up of Oi. As discussed above, the amount of isotopic O pile-up near Zn-terminated (0001) ZnO surfaces increases with temperature. In contrast, the pile-up remains almost constant near O-terminated (000$\bar{1}$) surfaces. An analytical model described in *Surface-Mediated Mechanisms for Defect Engineering in Metal Oxides*, the May, 2014 dissertation of Prashun Gorai, shows that the amount of pile-up may increase linearly with time and injection flux (F) (see FIG. 8), and may increase quadratically with the surface potential ($V_s$). Referring to FIG. 9, the activation energy for the buildup of surface potential ($V_s$) at the Zn-terminated surface is measured to be 1.7±0.3 eV. A widening of the space charge region occurs with increasing surface potential at the Zn-terminated surface, which is consistent with the behavior of an accumulation type space charge. $V_s$ remains almost constant at the O-terminated surface.

Various types of functional devices may be formed using a metal oxide single crystal having any of the physical and/or chemical characteristics described in this disclosure.

For example, the functional device may be a light emitting diode. The functional device may include a substrate in contact with the metal oxide single crystal, and one of the metal oxide single crystal and the substrate may be p-type, and the other may be n-type. In other words, the substrate may be p-type and the metal oxide single crystal may be n-type, or the substrate may be n-type and the metal oxide single crystal may be p-type. For example, a thin film or other nanostructure, such as a nanorod or nanotube, may comprise an n-type ZnO single crystal, and the p-type substrate may comprise a nitride semiconductor or a polymer. ZnO emits over a broad range of visible wavelengths, corresponding to a large number of different point defect states. O interstitials may be responsible for emission at yellow and orange wavelengths, and thus strong $O_i$ injection may produce increases in the yellow and orange emission lines under ultraviolet illumination. Strong $O_i$ injection may also affect the concentrations of other defects, and thus injecting $O_i$ at high rates may cause changes in the spectral shape of optical emission under ultraviolet illumination. Anion substitution for O in ZnO may hold promise for obtaining p-type ZnO, which could be important for producing full-color and pure-white LEDs.

In a second example, the functional device may be a display panel (e.g., liquid crystal display or plasma display panel) that may be used for computer and/or televisions screens. The display panel may comprise a stack of layers include a light emitting layer and a transparent electrode layer comprising the metal oxide single crystal. Currently, indium-tin oxide (ITO) is widely used as a transparent electrode in such devices; however, it would be beneficial to find alternatives given the limited availability of indium, as well as the desire for achieving higher conductivity at the same transparency level. Eliminating O vacancies by $O_i$ injection may improve the electron mobility in doped ZnO, thereby increasing its electrical conductivity and suitability for display applications. With respect to pure undoped ZnO, there is some disagreement about which defects are responsible for electrical conductivity. Leading candidates are Zn vacancies, Zn interstitials, and H as an unintentional impurity. It is surmised that the injection of $O_i$ at high rates to increase the concentration of interstitial oxygen may lead to increases in the electrical conductivity of undoped ZnO also.

In a third example, the functional device may be a solar cell. The functional device may comprise a stack of layers including a photoactive layer and a transparent electrode layer comprising the metal oxide single crystal. Highly-doped ZnO films have been shown to be useful in amorphous silicon and Cu(In,Ga)(S,Se)$_2$ solar cells.

In a fourth example, the functional device may be gas sensor formed by a nanorod comprising the metal oxide single crystal and having a first end connected to a first electrode and a second end connected to a second electrode. The ZnO gas sensor may be used to detect the presence of certain molecular species by exhibiting a change in electrical conductivity or another property. For example, electrical current may be passed through the nanorod when in the presence of a gas sample, and changes in the electrical conductivity may be measured.

Experimental Details

Wurtzite ZnO O-terminated (000$\bar{1}$) and Zn-terminated (0001) single crystals were obtained from CrysTeC GmbH.

All as-received samples had <0.5 nm root mean square surface roughness and were cut within 1° of the nominal surface orientation. Specimens were degreased by successive 5-min rinsing cycles in acetone, isopropanol and methanol and mounted for resistive heating on Si backing plates with Ta clips. A thick $SiO_2$ layer was thermally grown on the Si samples to prevent excessive sublimation of Si during annealing. Temperature was monitored with a chromel-alumel K-type thermocouple junction pressed onto the crystal surface. Distinguishing features of the experiments employed in this work were the ultrahigh vacuum character of the apparatus and the low $O_2$ pressures ($10^{-6}$-$10^{-5}$ torr) to promote surface cleanliness.

Oxygen diffusion rates were measured by exposing the ZnO samples to isotopically labeled oxygen gas at elevated temperatures. The wurtzite ZnO single crystals having a polar surface ((0001) or (000$\bar{1}$)) were annealed at elevated temperatures in the range of 540° C.-700° C. The annealing was carried out first in gaseous $O_2$ with a natural abundance of isotopes for four to six hours to achieve defect equilibrium (and eliminate sample to sample variation), and then in the isotopically labeled gas ($^{18}O_2$) for 90-105 min at the same temperature and oxygen partial pressure.

Diffused $^{18}O$ profiles were measured ex-situ with a PHI-TRIFT III time-of-flight secondary ion mass spectrometry (TOF-SIMS) using a cesium ion beam. To avoid strong mass interferences from water and hydroxyl-related radicals that have atomic masses similar to $^{18}O$ the ZnO samples were loaded in the SIMS chamber at least 8 hr prior to the profile measurements. This ensured enough time for the base or background pressure in the SIMS chamber to drop below $5 \times 10^{-8}$ torr, at which point mass interferences seemed to become negligible. Multiple measurements were made for each sample to rule out lateral variations in the diffusion profiles.

Although the present invention has been described in considerable detail with reference to certain embodiments thereof, other embodiments are possible without departing from the present invention. The spirit and scope of the appended claims should not be limited, therefore, to the description of the preferred embodiments contained herein.

All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A composition comprising an engineered defect concentration, the composition comprising:
   a metal oxide single crystal comprising a polar surface and having a bulk concentration of interstitial oxygen ($O_i$) of at least about $10^{14}$ atoms/cm³,
   wherein the polar surface comprises a concentration of impurity species of about 5% or less of a monolayer.

2. The composition of claim 1, wherein the concentration of impurity species is about 1% or less of a monolayer.

3. The composition of claim 1, wherein the metal oxide single crystal comprises ZnO, NiO, $LiCoO_2$, $KTaO_3$, or $SrTiO_3$.

4. The composition of claim 1, wherein the polar surface is cation-terminated.

5. The composition of claim 1, wherein the polar surface is anion-terminated.

6. The composition of claim 1, wherein the metal oxide single crystal comprises at least one linear dimension of about 100 nm or less, the metal oxide single crystal being nanostructured.

7. The composition of claim 1 comprising, when exposed to molecular oxygen at an elevated temperature, an oxygen diffusion profile having an exponential shape.

8. The composition of claim 7, wherein the oxygen diffusion profile comprises a near-surface pile-up region comprising an increased concentration of the interstitial oxygen ($O_i$), the near-surface pile-up region being within about 40 nm of the polar surface.

9. A functional device comprising the composition of claim 1.

10. The functional device of claim 9 being selected from the group consisting of: a light emitting diode, a solar cell, a display panel and a gas sensor.

* * * * *